(12) United States Patent
Murray et al.

(10) Patent No.: US 10,743,860 B2
(45) Date of Patent: Aug. 18, 2020

(54) METHODS AND DEVICES FOR PASSING SUTURES AROUND ANATOMICAL STRUCTURES

(71) Applicant: Medos International Sarl, Le Locle (CH)

(72) Inventors: Meghan P. Murray, Livonia, MI (US); Allison Stocks, Medford, MA (US); Ariel L. Leigh, Seattle, WA (US); Alexandra Tsoi, Fort Collins, CO (US); Mary Schmidt, Boston, MA (US)

(73) Assignee: DEPUY SYNTHES PRODUCTS, INC., Raynham, MA (US)

( * ) Notice: Subject to any disclaimer, the term of this patent is extended or adjusted under 35 U.S.C. 154(b) by 232 days.

(21) Appl. No.: 15/725,882

(22) Filed: Oct. 5, 2017

(65) Prior Publication Data

US 2018/0028178 A1 Feb. 1, 2018

Related U.S. Application Data

(62) Division of application No. 14/037,822, filed on Sep. 26, 2013, now Pat. No. 9,808,237.

(51) Int. Cl.
*A61B 17/04* (2006.01)
*A61B 17/00* (2006.01)

(52) U.S. Cl.
CPC ...... *A61B 17/0469* (2013.01); *A61B 17/0482* (2013.01); *A61B 2017/00867* (2013.01)

(58) Field of Classification Search
CPC ............ A61B 17/0469; A61B 17/0483; A61B 17/0485; A61B 2017/00349; A61B 17/0482; A61B 2017/00867; A61B 17/06109; A61B 2017/06019
See application file for complete search history.

(56) References Cited

U.S. PATENT DOCUMENTS

| | | | |
|---|---|---|---|
| 5,447,512 A | 9/1995 | Wilson et al. |
| 5,573,542 A | 11/1996 | Stevens |
| 7,048,747 B2 | 5/2006 | Arcia et al. |
| 7,842,050 B2 | 11/2010 | Diduch et al. |
| 8,029,518 B2 | 10/2011 | Goldfarb et al. |
| 8,267,948 B2 | 9/2012 | Marshall et al. |
| 9,808,237 B2 | 11/2017 | Murray et al. |

(Continued)

*Primary Examiner* — Katherine M Shi (57) ABSTRACT

Various exemplary methods and devices are provided for passing sutures around anatomical structures. In an exemplary embodiment, a suture delivery device is provided that includes a body portion having a suture delivery member disposed therein and configured to pass a suture around an anatomical structure. The suture delivery member can be movable between a retracted configuration in which the suture delivery member is disposed within the body portion and an advanced configuration in which the suture delivery member extends distally beyond the body portion and assumes an arcuate shape. The arcuate shape can correspond to a shape of the anatomical structure and can extend almost all of the way around the anatomical structure, for example at least around 270° of a circle, thus assisting a user in passing the suture around the anatomical structure without having to manually manipulate the suture delivery device at awkward angles around adjacent tissue.

8 Claims, 10 Drawing Sheets

(56) References Cited

U.S. PATENT DOCUMENTS

| | | |
|---|---|---|
| 2001/0012945 A1 | 8/2001 | Romano |
| 2002/0147456 A1 | 10/2002 | Diduch et al. |
| 2007/0118142 A1* | 5/2007 | Krueger ............. A61B 17/8819 606/92 |
| 2010/0016899 A1* | 1/2010 | Gelfand ............. A61B 17/0401 606/280 |
| 2010/0145364 A1 | 6/2010 | Keren et al. |
| 2011/0028995 A1 | 2/2011 | Miraki et al. |
| 2011/0245850 A1 | 10/2011 | van der Burg et al. |
| 2012/0016385 A1 | 1/2012 | Keren et al. |
| 2014/0249530 A1* | 9/2014 | Babikian ................ A61B 17/82 606/74 |
| 2015/0032169 A1* | 1/2015 | Holowecky .......... A61B 17/842 606/328 |

\* cited by examiner

METHODS AND DEVICES FOR PASSING SUTURES AROUND ANATOMICAL STRUCTURES

CROSS REFERENCE TO RELATED APPLICATIONS

The present application is a divisional of U.S. patent application Ser. No. 14/037,822 entitled "Methods and Devices for Passing Sutures Around Anatomical Structures" filed Sep. 26, 2013, which is hereby incorporated by reference in its entirety.

FIELD

The present disclosure relates generally to methods and devices for passing sutures around anatomical structures.

BACKGROUND

The complete or partial detachment of ligaments, tendons and/or other soft tissues from their associated bones within the body are commonplace injuries, particularly among athletes. Such injuries generally result from excessive stresses being placed on these tissues. By way of example, tissue detachment may occur as the result of an accident such as a fall, over-exertion during a work-related activity, or during the course of an athletic event. In the case of a partial detachment, the injury will frequently heal itself, if given sufficient time and if care is taken not to expose the injury to further undue stress. In the case of complete detachment, however, surgery is often needed to re-attach the soft tissue to its associated bone.

Conventional surgical procedures for repairing soft tissue detachment, e.g., ligament detachment, can employ a ligament graft to replace one or more torn ligaments. If a ligament graft is used, it can be attached to a bone using one or more sutures, which therefore must be passed around the bone to attach the ligament thereto. Passing the one or more sutures around the bone can be a time-consuming and difficult portion of the surgery, since conventional tools for passing suture around bone require the surgeon to approach the bone at an awkward angle and are often not customized for use with complex anatomies. Manipulating around complex anatomical structures can be even more difficult in minimally invasive surgery. In conventional minimally invasive procedures, surgical tools must be inserted through one or more small incisions, thus limiting visibility of the surgical site and a surgeon's ability to manipulate the surgical tools at varying angles.

Figure 1A:
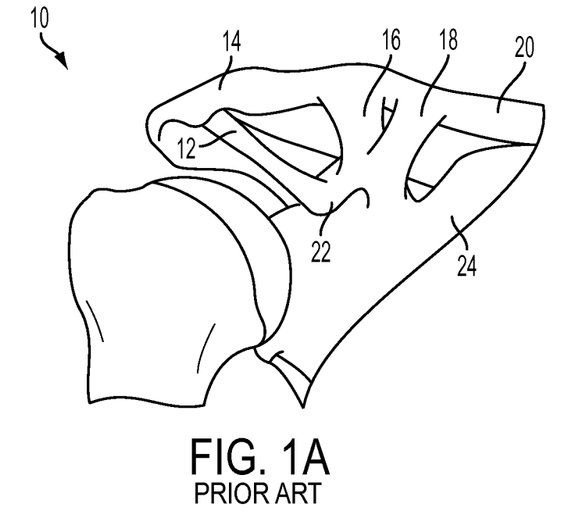
FIG. 1A (PRIOR ART) is a perspective view of a healthy AC joint.
Figure 1B:
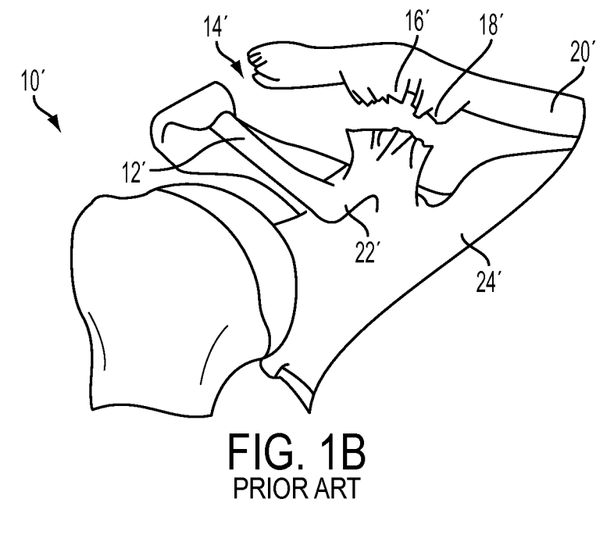
FIG. 1B (PRIOR ART) is a perspective view of a torn AC joint having undergone AC separation.

For example, one common injury is acromioclavicular ("AC") separation, in which one or more ligaments connecting the clavicle to the scapula are torn, typically by blunt force trauma. FIG. 1A shows a healthy AC joint 10, with a coraco acromial ligament 12, an acromio clavicular ligament 14, and coraco clavicular ligaments 16, 18 intact. As shown, each of the ligaments 12, 14, 16, 18 connect a clavicle 20 to a scapula 24, in particular to a coracoid process 22. FIG. 1B shows a grade III torn AC joint 10' having undergone AC separation, in which an acromio clavicular ligament 14' and coraco clavicular ligaments 16', 18' have been torn, thus partially severing the connection of a clavicle 20' to a scapula 24'. This condition can result in severe pain, swelling, and bruising.

Severe AC separations, such as the grade III separation shown in FIG. 1B, can be repaired surgically using an anatomical coracoclavicular repair ("ACCR") technique. Conventional ACCR methods can employ a ligament graft and at least one suture affixed thereto to reattach the clavicle 20' to the scapula 24'. To fix the ligament graft to the scapula 24', a surgeon must typically wrap the ligament graft around the coracoid process 22' by first manipulating the suture around the coracoid process 22'. However, conventional tools for passing the suture around the coracoid process 22' can require a surgeon to manually manipulate the suture around the coracoid process 22', which can involve manipulating a rigid tool at awkward angles in tight spaces. This can lead to an increased risk of tissue damage and can increase surgical time.

Accordingly, there remains a need for improved methods and devices for passing sutures around anatomical structures.

SUMMARY

The present invention generally provides methods and devices for passing sutures around anatomical structures. In one aspect, a suture delivery device is provided that has a body portion with a lumen formed therein and extending along at least a portion of a longitudinal axis thereof, an actuation member operatively associated with the body portion, and a suture delivery member that can have a suture retaining feature thereon. The suture delivery member can be deployable from a distal end of the body portion and can be selectively movable by the actuation member from a retracted configuration to an advanced configuration. The suture delivery member can also have a distal end that is pre-shaped in an arc that defines at least about 270° of a circle, about 270° to about 310° of a circle, or about 310° of a circle.

The body of the suture delivery device can include a proximal handle and a distal shaft. The distal shaft can have a lumen extending therethrough and can have a distal end that is curved. In one aspect, the lumen can extend through an entire length of the body portion, and/or the suture can extend through the lumen.

The suture delivery member can be formed in a variety of ways. In one aspect, the suture delivery member can be formed from a shape memory material. The shape memory material can be one of a copper-zinc-aluminum-nickel alloy, a copper-aluminum-nickel alloy, and a nickel-titanium alloy. The suture delivery member can have a suture retaining feature formed on a distal end thereof, which can be a notch.

In one embodiment, the actuation member can be a plunger. The plunger can include a depth indication feature for measuring a length of the suture delivery member extending beyond the distal end of the body portion. Additionally or alternatively, the plunger can include a direction indication feature that indicates a direction of curvature of the arc of the suture delivery member. Similarly, the handle can include a direction indication feature that indicates a direction of curvature of the arc.

In another aspect, a method for passing a suture around an anatomical structure is provided that includes inserting a suture delivery device into a body of a patient such that a distal end of a the suture delivery device is positioned adjacent to a bony structure, advancing a suture delivery member carrying a suture from within the suture delivery device such that the suture delivery member follows an arc defining at least about 270° of a circle to extend around the bony structure, manipulating the suture to engage the bony structure, and passing the suture through a soft tissue. The method can further include, after manipulating the suture to engage the bone, releasing the suture from the suture delivery device. Additionally or alternatively, the method can further include attaching the suture to a ligament graft and securing the ligament graft to the bone using the suture. The bone can comprise the coracoid process and/or the ligament graft can be used to repair a torn acromioclavicular joint.

BRIEF DESCRITION OF DRAWINGS

This invention will be more fully understood from the following detailed description taken in conjunction with the accompanying drawings, in which.

DETAILED DESCRIPTION

Certain exemplary embodiments will now be described to provide an overall understanding of the principles of the structure, function, manufacture, and use of the methods and devices disclosed herein. One or more examples of these embodiments are illustrated in the accompanying drawings. Those skilled in the art will understand that the methods and devices specifically described herein and illustrated in the accompanying drawings are non-limiting exemplary embodiments and that the scope of the present invention is defined solely by the claims. The features illustrated or described in connection with one exemplary embodiment may be combined with the features of other embodiments. Such modifications and variations are intended to be included within the scope of the present invention Further, in the present disclosure, like-numbered components of the embodiments generally have similar features, and thus within a particular embodiment each feature of each like-numbered component is not necessarily fully elaborated upon. Additionally, to the extent that linear or circular dimensions are used in the description of the disclosed systems, devices, and methods, such dimensions are not intended to limit the types of shapes that can be used in conjunction with such systems, devices, and methods. A person skilled in the art will recognize that an equivalent to such linear and circular dimensions can easily be determined for any geometric shape. Sizes and shapes of the systems and devices, and the components thereof, can depend at least on the anatomy of the subject in which the systems and devices will be used, the size and shape of components with which the systems and devices will be used, and the methods and procedures in which the systems and devices will be used.

Various exemplary methods and devices are provided for passing sutures around anatomical structures. In an exemplary embodiment, shown in FIG. 2, a suture delivery device 100 is provided that includes a body portion 102 having a suture delivery member 104 disposed therein and configured to pass a suture 106 (FIG. 3) around an anatomical structure. Upon actuation of an actuation member 108 disposed on the body portion 102, the suture delivery member 104 can be moved between a retracted configuration (FIG. 11) in which the suture delivery member 104 is disposed within the body 102 and an advanced configuration (FIGS. 2 and 12) in which the suture delivery member 104 extends distally beyond the body 102. In the advanced configuration, at least a distal portion 110 of the suture delivery member 104 can be preconfigured to assume an arcurate shape that facilitates passage of the suture 106, which may be attached thereto, around the anatomical structure. The curvature of the arcurate shape can correspond to a curvature of the anatomical structure and can extend almost all of the way around the anatomical structure, for example at least around 270° of a circle. The arcurate shape of the distal portion 110 can thus assist a user in locating the anatomical structure and in passing the suture 106 around the anatomical structure without having to manually manipulate the suture delivery device 100 at awkward angles around adjacent soft and/or bony tissue, thus reducing surgical time and a risk of injury to the adjacent tissue.

The body portion 102 can be of any shape and size to facilitate gripping of a proximal portion of the suture delivery device 100 and insertion of at least a distal portion of the suture delivery device 100 into a body of a patient. In an exemplary embodiment, shown in FIGS. 2-4, the body portion 102 can include a handle 112 for gripping and a shaft 114 extending distally therefrom for insertion into the patient's body. Although the handle 112 and the shaft 114 are shown to be elongate and aligned along a longitudinal axis L in the illustrated embodiment, it will be appreciated by a person skilled in the art that any portion of the body 102 can be offset from any one or more portions to facilitate manipulation of the suture delivery device 100 around anatomical structures. By way of non-limiting example, a longitudinal axis of the handle 112 can be offset from a longitudinal axis of the shaft 114. Also to facilitate manipulation of the suture delivery device 100 around anatomical structures, in particular around soft tissue, one or more edges of the body portion 102 can be chamfered. The chamfered edges can reduce a risk of damage to surrounding tissue as the suture 106 is delivered to a desired anatomical site and can also facilitate comfortable gripping of the suture delivery device 100 by the user.

Figure 2:
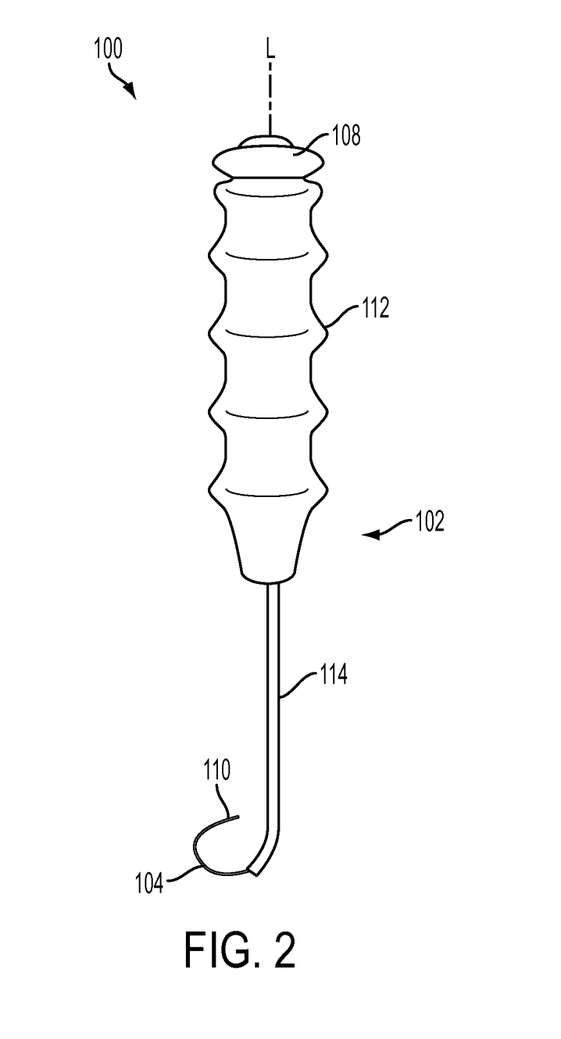
FIG. 2 is a side view of one embodiment of a suture delivery device.
Figure 3:
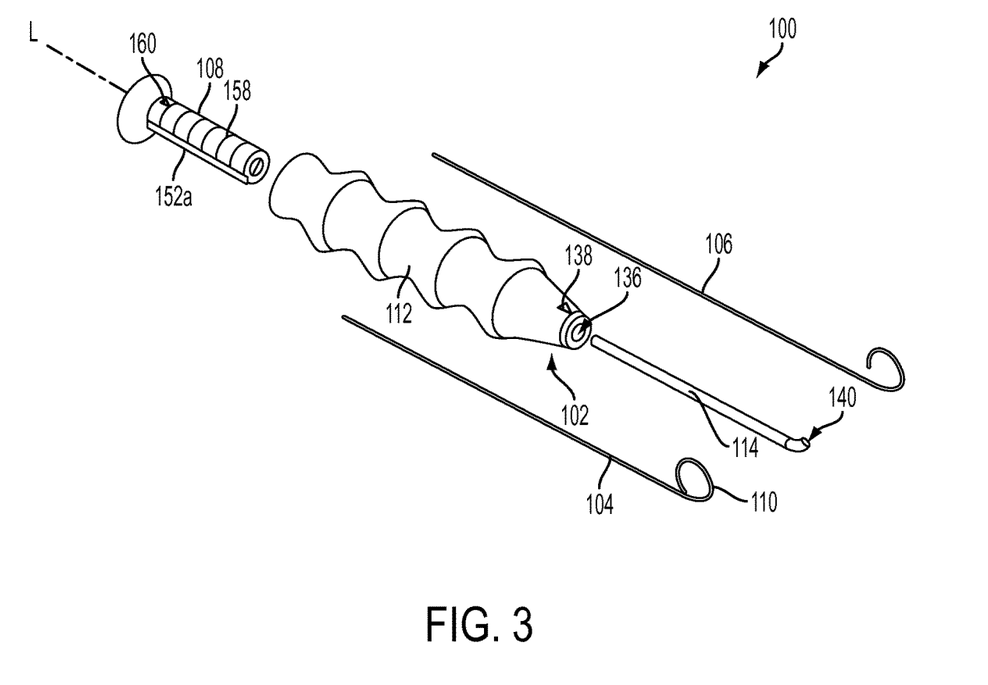
FIG. 3 is an exploded view of the suture delivery device of FIG. 2.
Figure 4:
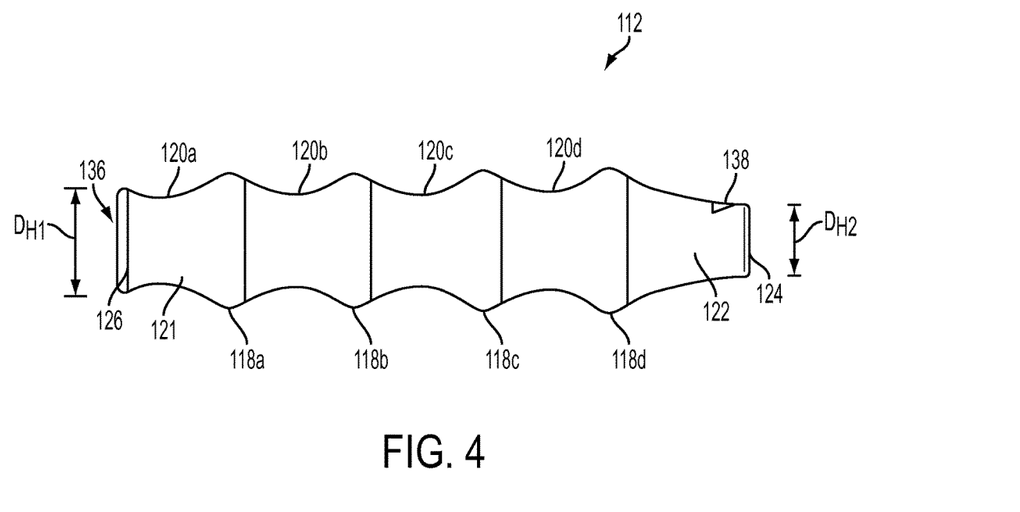
FIG. 4 is a side view of a handle of the suture delivery device of FIG. 2.

With reference to FIGS. 2-4, the handle 112 can be a generally elongate member having a proximal portion 121 and a distal portion 122. The handle 112 can be configured in a variety of ways to improve the user's ability to deliver and/or position the suture 106 around the anatomical structure. For example, the handle 112 can have various features thereon to facilitate gripping, at least along the proximal portion 121 thereof, and/or can be formed from one or more materials that facilitate gripping. In an exemplary embodiment, shown in FIG. 4, the handle 112 can have multiple ridges, each separated by a valley. Although any number of ridges and valleys can be used, one can utilize from one to about five ridges. In an exemplary embodiment, four ridges 118a, 118b, 118c, and 118d are separated by four valleys 120a, 120b, 120c, 120d formed therebetween. Each of the valleys 120a, 120b, 120c, 120d can be configured for gripping by one or more fingers of the user. Each of the ridges 118a, 118b, 118c, and 118d can extend radially outward from the longitudinal axis L and any circumferential length around the handle 112, although in an exemplary embodiment the ridges 118a, 118b, 118c, and 118d extend around an entire circumferential length of the handle 112. One skilled in the art will appreciate that there can be any number of ridges and valleys spaced at any distance apart from one another sufficient to accommodate one or more figures of a user within each of the valleys 120a, 120b, 120c, 120d. Any combination of the ridges 118a, 118b, 118c, and 118d and the valleys 120a, 120b, 120c, 120d, e.g., the ridge 118a and the valley 120a, can form a separable unit that is removably attachable to the remaining portion of the handle 112, e.g., by screwing, snap-fit, or any other attachment means, to allow the user to adjust a length of the handle 112 based on, e.g., a desired depth of insertion of the suture delivery device 100 and/or a size of the user's hand. Alternatively, as in the illustrated embodiment, the handle 112 can be an integrally formed unit.

To further facilitate suture delivery, a portion of the suture delivery device 100, such as the distal portion 122 of the handle 112, can have at least one direction indication feature formed thereon that provides information about an orientation of the distal portion of the suture delivery device 100 to the user, which can be useful when the distal portion of the suture delivery device 100 is inserted through an incision into the patient's body and is not visible to the user. In the illustrated embodiment, an arrow 138 etched along a distal portion 122 of the handle 112 can indicate a direction of curvature of the suture delivery member 104 when in the advanced configuration. Thus, the user can know the direction of the suture delivery member 104 within the patient's body without being able to see the suture delivery member 104. This feature can be particularly useful for minimally invasive surgical procedures, in which the suture delivery device 100 is inserted through a portal to minimize trauma incurred by the surgery. It will be appreciated by a person skilled in the art that the direction indication feature could be any etching or marking on an exterior surface of the proximal portion of the suture delivery device 100 and can indicate any type of information about the distal portion of the instrument 100 that is configured for insertion into the body.

As noted above, the handle 112 can be generally elongate, but it can have any shape suitable to its intended use. In one embodiment, shown in FIG. 4, the distal portion 122 of the handle 112 is tapered to facilitate improved visibility and/or to make it possible for a portion of the handle 112 to be inserted into a portal or an incision in the patient's body. The degree of tapering can vary, but in the illustrated embodiment the distal portion 122 tapers such that a distal-facing wall 124 of the handle 112 has a diameter $D_{H2}$ that is smaller than a diameter $D_{H1}$ of a proximal-facing wall 126 of the handle 112. Furthermore, as mentioned above, various edges of the handle 112 can be chamfered to facilitate both safe insertion into the patient's body and comfortable gripping by the user. For example, the proximal-facing wall 126 of the handle 112, shown in FIG. 5, can have an outer chamfered edge 128 and an inner chamfered edge 130, and the distal-facing wall 124, shown in FIG. 6, can have an outer chamfered edge 132 and an inner chamfered edge 134.

The handle 112 can have any length suitable for gripping and handling, as will be appreciated by a person skilled in the art. Generally, however, the length of the handle 112 can be in the range of about 3 inches to 6 inches and a cross-sectional dimension of the handle 112 can be in the range of about 0.5 inches to 2 inches.

As noted above, the body portion 102 further includes a shaft 114 that extends distally from the handle 112. The shaft 114 can be configured in a variety of ways such that it is suitable for insertion into a body of a patient. In the illustrated embodiment, shown in FIGS. 2, 3, and 7, the shaft 114 is a generally elongate tube having a substantially uniform, circular cross-section with an outer diameter $D_{SO}$ along an entire length thereof, although it will be appreciated by a person skilled in the art that the shaft 114 can have any cross-sectional shape and size, either constant or varying, along any length thereof. The outer diameter $D_{SO}$ and a length of the shaft 114 can be of any size suitable for insertion into the patient's body, although generally the diameter $D_{SO}$ can be in the range of about 2 mm to 8 mm and the length of the shaft 114 can be in the range of about 3 inches to 8 inches. The shaft 114 can be made of any one or more materials suitable for insertion in the patient's body, e.g., stainless steel. In some embodiments, a distal portion 148 of the shaft 114 can be formed from a more flexible material than a proximal portion 146 of the shaft 112 to help the user manipulate the shaft 114 around delicate anatomical structures effectively but with a reduced risk of damage. Also, similarly to the handle 112, the shaft 114 can have chamfered edges to reduce a risk of harm to surrounding tissue during insertion into the patient's body.

Figure 7:
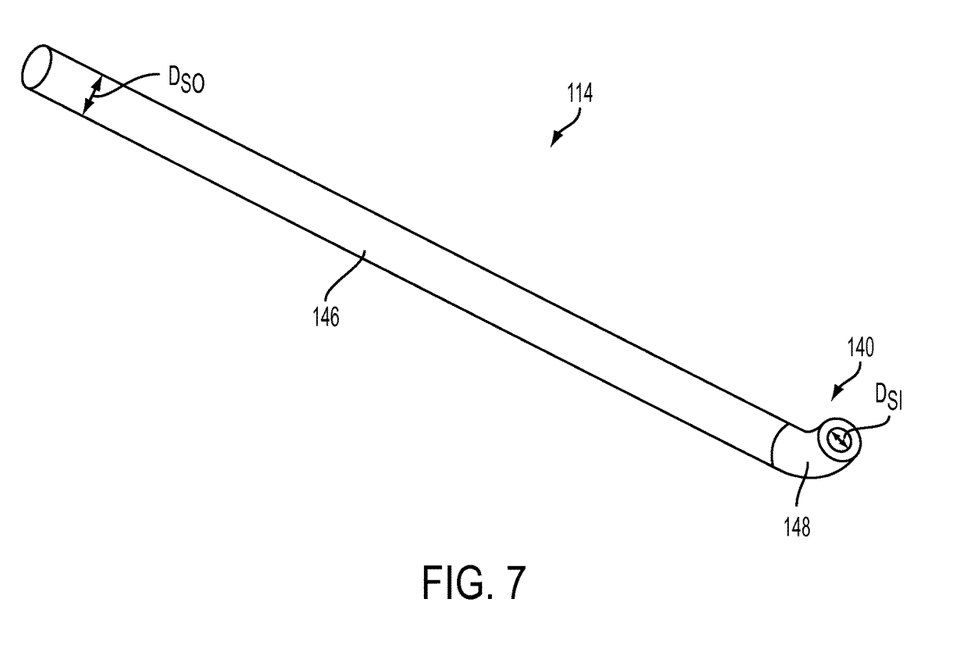
FIG. 7 is a perspective view of a shaft of the suture delivery device of FIG. 2.

The shaft 114 can have one or more features thereon to assist a surgeon in locating a desired anatomical structure and/or in stabilizing the suture delivery device 100 against the desired anatomical structure. For example, the distal portion 148 of the shaft 114 can be curved or angled with respect to the longitudinal axis L. A radius of curvature of the distal portion 148 can vary. By way of non-limiting example, the radius of curvature of the distal portion 148 can be about 0.5 inches.

As explained below, a passageway can extend through any length of the body portion 102 for seating the suture 106 and various elements therein. By way of non-limiting example, the passageway can extend through both the handle 112 and the shaft 114, from a proximal-most end of the handle 112 to a distal-most end of the shaft 114, to form a continuous passageway through the body 102. The passageway can have any cross-sectional shape and any size, either constant or varying along a longitudinal length thereof, sufficient to accommodate one or more of the actuation member 108, the suture delivery member 104, and the suture 106 therein. In an exemplary embodiment, the passageway has a generally circular cross-section along an entire length thereof with a first diameter along a proximal portion that is large enough to accommodate the actuation member 108 and a second diameter along the distal portion that is smaller than the first diameter, but large enough to accommodate the suture delivery member 104 therein. In addition, the first and second diameters of the passageway can be large enough to slidably seat the suture 106 through any length thereof, either adjacent to or within the actuation member 108 and/or the suture delivery member 104.

With reference to FIGS. 3-7, the passageway can extend through more than one element of the suture delivery device 100 and can be formed from various discrete channels. In the illustrated embodiment, a proximal portion of the passageway runs through a channel 136 of the handle 112 and a distal portion of the passageway runs through a channel 140 of the shaft 114. The channel 136 can have any cross-sectional shape and any size, although in the illustrated embodiment the channel 136 has a generally circular cross-sectional shape and is configured for seating the actuation member 108 in a proximal portion thereof and the shaft 114 in a distal portion thereof. Accordingly, a diameter of the channel 136 decreases from a proximal end of the channel 136 to a distal end of the channel 136, either constantly or in a step-wise manner, such that the proximal end of the channel 136 is configured to seat at least a portion of the actuation member 108 and the distal end of the channel 136 is configured to seat at least a portion of the shaft 114. Accordingly, a diameter $D_{HP}$ of the proximal opening 142 of the channel 136 can be larger than a diameter $D_{HD}$ of the distal opening 144 of the channel 136. In particular, the diameter $D_{HP}$ of the proximal opening 142 can be larger than a diameter of at least a distal portion of the actuation member 108 and the diameter $D_{HD}$ of the distal opening 144 can be larger than the outer diameter $D_{SO}$ the shaft 114.

In the illustrated embodiment, the channel 136 forms a continuous passageway from the proximal-most end of the handle 112 to a distal-most end of the handle 112, although it will be appreciated by a person skilled in the art that the channel 136 can extend through any portion of the handle 112. In an alternative embodiment, not shown, the handle 112 can have multiple channels for seating different features, e.g., a channel for seating the actuation member 108 and a channel for seating the shaft 114.

The channel 136 of the handle 112 can be configured to mate with the shaft 114 and the actuation member 108 in a variety of ways. In an exemplary embodiment, the diameter $D_{SO}$ of the shaft 114 and the diameter $D_{HD}$ of the distal opening 144 of the channel 136 can be sized to allow for compression or interference fit of the shaft 114 to the handle 112, thus preventing relative movement between the shaft 114 and the handle 112. Although in some embodiments the shaft 114 can rotate or slide relative to the handle 112, for example to adjust an orientation or a length of the suture delivery device 100, in the illustrated embodiment a fit between the shaft 114 and the handle 112 prohibits any movement of the shaft 114 with respect to the handle 112. In an alternative embodiment, the shaft 114 can be constructed so as to be unitary or integral with the handle 112.

Figure 5:
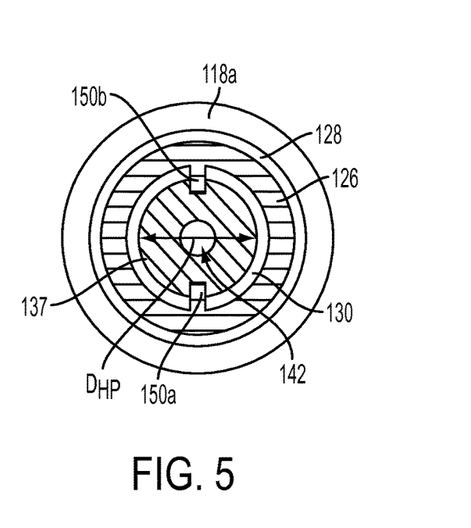
FIG. 5 is a proximal end view of the handle of FIG. 4.
Figure 6:
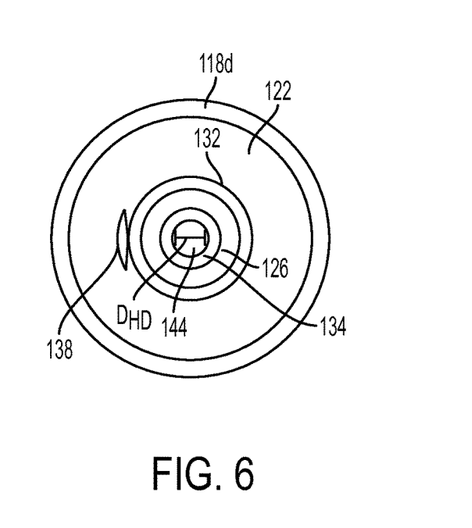
FIG. 6 is a distal end view of the handle of FIG. 4.

By contrast, the channel 136 can be configured to mate with the actuation member 108 such that the actuation member 108 is slidable within the channel 136 but can be prohibited from rotation within the handle 112. In the exemplary embodiment, as shown in FIG. 5, the actuation member 108 is prevented from rotating within the handle 112 by first and second ridges 150a, 150b that extend radially inward from an inner wall 137 of the handle 112 and are configured to engage first and second notches 152a, 152b of the actuation member 108. Although there are two, generally rectangular ridges 150a, 150b in the illustrated embodiment, there can be any number of ridges of any shape and size, same or different from one another. The ridges 150a, 150b can have any longitudinal length suitable for engagement with the actuation member 108, for example the ridges 150a, 150b can be formed only along a proximal portion of the channel 136. The handle 112 can also have a stop mechanism (not shown), for example a protrusion extending radially inward from the inner wall 137 of the handle 112 along a proximal portion thereof to prevent the actuation member 108 from falling out of the handle 112. In another embodiment, the relative proportions of the ridges 150a, 150b and the notches 152a, 152b can change along proximal-most ends thereof to create a tighter fit between the ridges 150a, 150b and the notches 152a, 152b that prevents further proximal movement. By way of non-limiting example, the proximal-most ends of the ridges 150a, 150b can extend radially inward to a depth that is greater than a depth of the proximal-most ends of the notches 152a, 152b, thus preventing proximal movement of the actuation member 108 beyond a desired distance. Additionally or alternatively, there can also be a second stop mechanism along a distal end of the handle 112 to prohibit distal movement of the actuation member 108 beyond a desired distance into the handle 112 and therefore a desired distance that the suture delivery member 104 extends beyond the body portion 102.

Like the channel 136 of the handle 112, the channel 140 of the shaft 114 can have any cross-sectional shape and any diameter, although in the illustrated embodiment the channel 140 has a generally circular cross-sectional shape and a constant diameter $D_{SI}$ along an entire length thereof. The channel 140 can form a continuous passageway from a proximal-most end of the shaft 114 to the distal-most end of the shaft 114, although the channel 140 can extend along any length of the shaft 114. At least a distal portion of the channel 140 can be configured to slidably seat the suture delivery member 104. In particular, the diameter $D_{SI}$ of the channel 140 can be larger than an outer diameter $D_D$ of the suture delivery member 104, at least along the distal portion of the channel 140.

Figure 8:
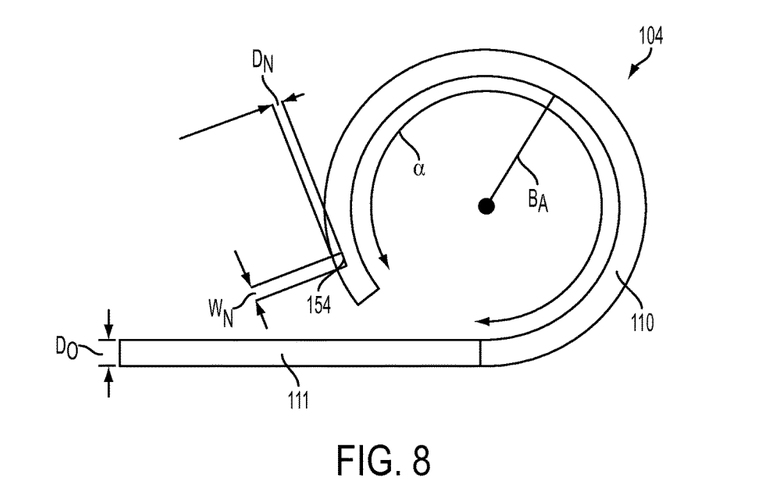
FIG. 8 is a partial side view of a suture delivery member of the suture delivery device of FIG. 2.

The suture delivery member 104 can be configured to be slidably seated within at least a portion of the channel 136 of the handle 112 and the channel 140 of the shaft 114. As shown in FIGS. 2, 3, and 8, in an exemplary embodiment the suture delivery member 104 is a solid, generally elongate structure that can be small enough to fit within the channel 136 and the channel 140. The suture delivery member 104 can have any longitudinal length suitable for insertion into the patient's body. By way of non-limiting example, the diameter $D_D$ of the suture delivery member 104 can be in the range of about 0.015 inches to 0.100 inches, and the length of the suture delivery member 104 can be in the range of about 4 inches to 8 inches. In the illustrated embodiment, the suture delivery member 104 extends through both the handle 112 and the shaft 114 in both the retracted and advanced configurations.

Figure 8A:
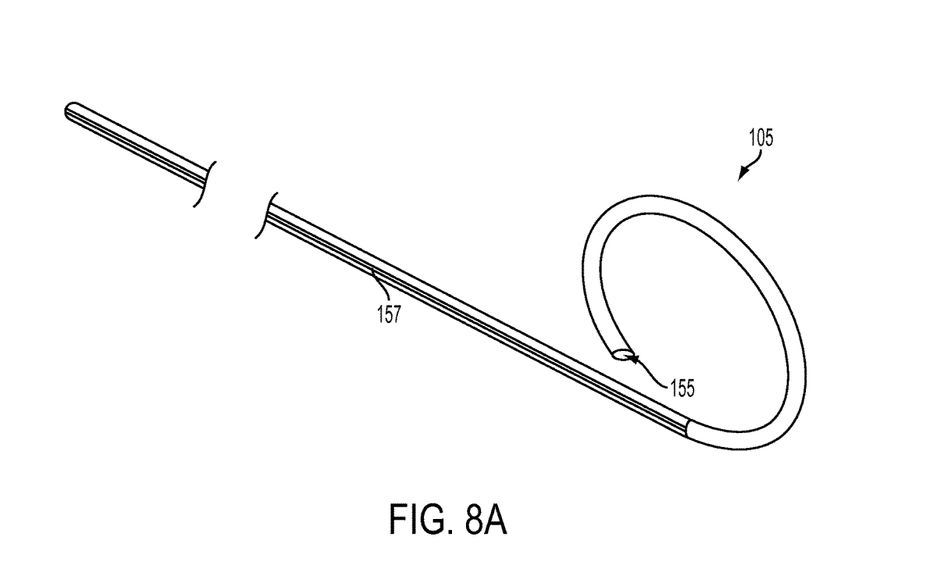
FIG. 8A is a perspective view of another embodiment of a suture delivery member.

The suture delivery member 104 can be configured to engage one or more sutures in a variety of ways. In the illustrated embodiment, the suture delivery member 104 has a suture-engaging notch 154 formed on a distal portion 110 thereof. Because the notch 154 of the illustrated embodiment is formed on a distal tip of the distal portion 110, the suture 106 can be passed around an anatomical structure substantially as far as the suture delivery member 104 extends around the anatomical structure in the advanced configuration. The notch 154 can be configured to engage the suture 106 directly and/or it can be configured to engage a corresponding engagement feature of the suture 106. Accordingly, the notch 154 can have a width $W_N$ and a depth $D_N$ suitable for wrapping of the suture 106 therearound at least one time, and/or for mating with the corresponding engagement feature of the suture 106. By way of non-limiting example, the corresponding engagement feature of the suture 106 can a needle (not shown) through which the suture 106 is threaded and which is configured to engage the notch 154 by, e.g., snap-fit, compression fit, etc. The notch 154 can grasp the suture 106 along any portion thereof, for example along a central portion thereof, such that at least the central portion of the suture 106 is retracted inside the channel 140 of the shaft 114 when the suture delivery member 104 is in the retracted position. One or more trailing ends of the suture 106 can extend through the channels 140, 136 adjacent to the suture delivery member 104. In another embodiment, shown in FIG. 8A, the suture delivery member 104 can have a lumen 155 formed through any length thereof to allow for threading of the suture 106 through the lumen 155. Additionally or alternatively, the suture delivery member 104 can have a longitudinal groove 157 formed through any length of an exterior sidewall thereof. The lumen 155 and/or the groove 157 can each have a size sufficient to slidably seat one or more sutures extending longitudinally therethrough.

As mentioned above, the suture delivery member 104 extends through the body portion 102 and can be configured to move between the retracted configuration and the advanced configuration as a result of attachment to the actuation member 108. In the illustrated embodiment, the suture delivery member 104 slides along the longitudinal axis L to move proximally to the retracted configuration and distally to the advanced configuration. In the retracted configuration, an entire length, or substantially the entire length, of the suture delivery member 104 can be enclosed within the channel 136 and the channel 140. The suture delivery member 104 can be disposed in the retracted configuration during insertion into the patient's body, thus protecting the suture delivery member 104 from exposure to tissue. In the advanced configuration, at least the distal portion 110 of the suture delivery member 104 can extend distally beyond a distal-most end of the body portion 102 to deliver the suture 106, which can be attached thereto, around an adjacent anatomical structure. Between the retracted and advanced configurations, the suture delivery member 104 can assume one of many intermediate configurations in which the distal portion 110 of the suture delivery member 104 extends any distance beyond the distal-most end of the body portion 102 that is shorter than a distance that the suture delivery member 104 extends beyond the distal-most end of the body portion 102 in the advanced configuration.

In the advanced configuration, at least the distal portion 110 of the suture delivery member 104 can be preconfigured to an arcuate shape suitable for passing the suture 106 around an anatomical structure. That is, the distal portion 110 is biased to an arcuate shape. Inner walls of the shaft 114 constrain the distal portion 110 in the retracted configuration, causing the distal portion 110 to be substantially straight. However, when advanced beyond the shaft 114, the distal end 110 is free to assume its arcuate shape. An arc $\alpha$ defined by the distal portion 110 in the advanced configuration can extend around less than 360° of a circle, for example around about 270° of a circle or between about 270° of a circle and about 310° of a circle. This can allow a user to pass the suture 106, which can be attached to the suture delivery member 104, almost all the way around the anatomical structure simply by deploying the suture delivery member 104 to the advanced configuration when it is positioned adjacent to the anatomical structure. That the arc $\alpha$ does not form a closed circle in the advanced configuration, or in any intermediate configuration, can facilitate grasping of the suture 106 from the suture delivery member 104 once the suture delivery member 104 has been deployed by reducing a risk of the suture 106 catching on a proximal portion 111 of the suture delivery member 104 and leaving a gap between adjacent portions of the suture delivery member 104 to allow for insertion of a grasping tool. A radius $R_A$ of the arc $\alpha$ can be substantially the same as a radius of the anatomical structure, such that the suture delivery member 104 is customized for use with a particular anatomical structure and can pass closely around the anatomical structure without running into nearby anatomical structures or tissue. Moreover, although the arc $\alpha$ of the illustrated embodiment is substantially circular, the arc $\alpha$ can assume any shape to follow the curvature of the anatomical structure as closely as possible, which can optimize the suture delivery device 100 for use particularly in complex anatomies where the user is operating in tight spaces.

The arc $\alpha$ of the suture delivery member 104 can be configured to extend in any direction. As is clear from FIG. 3, a direction of curvature of the arc $\alpha$ can be the same as a direction of curvature of the distal portion 140 of the shaft 114, such that the arc $\alpha$ merely completes the portion of the circle formed by the distal portion 140 of the shaft 114. In this way, the shaft 114 can help to direct the direction of curvature of the suture delivery member 104 in the advanced configuration. As mentioned above, the direction of the arc $\alpha$ can be indicated by one or more direction indication features, for example the arrow 138 on the handle 112. Specifically, in the illustrated embodiment, the arc $\alpha$ curves back towards a sidewall on which the arrow 138 is etched.

The distal portion 110 of the suture delivery member 104 can be configured to assume the arcuate shape in a variety of ways. In some embodiments, the suture delivery member 104 can be formed from a shape memory material, which can include a single material or any combination of materials, such that at least the distal portion 110 of the suture delivery member 104 is curved in the arcuate shape when in a resting configuration. Non-limiting examples of shape memory materials include copper-zinc-aluminum-nickel alloys, copper-aluminum-nickel alloys, nickel-titanium alloys such as Nitinol, thermoplastic materials such as Nylon or Nylon blends, and shape memory polymers such as Veriflex™. The shape memory material can facilitate the suture delivery member 104 being biased to the arcuate shape. The shape memory material can facilitate advancement of the suture delivery member 104 into tissue by allowing the suture delivery member 104 to be deformed or bent in the retracted configuration in which the suture delivery member 104 has a smaller width than a width thereof in the advanced configuration, while also allowing the suture delivery member 104 to automatically move from the retracted configuration to the advanced configuration. In an exemplary embodiment, the entirety of the suture delivery member 104 can be formed from one or more shape memory materials. In another exemplary embodiment, only the distal portion 110 of the suture delivery member 104 can be formed from one or more shape memory materials, and another portion of the suture delivery member 104, e.g., an intermediate portion from which the distal portion extends, can be formed of a non-shape memory material, e.g., titanium, stainless steel, etc.

Figure 9:
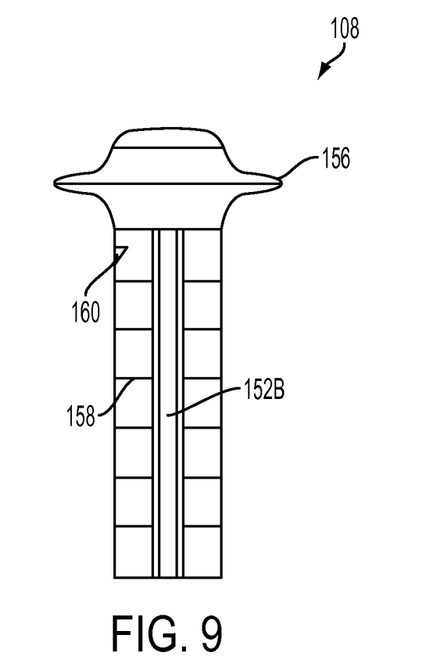
FIG. 9 is a side view of an actuation member of the suture delivery device of FIG. 2.

The actuation member 108 can be any type of actuation member configured for manual actuation that functions to move the suture delivery member 104 between the advanced and retracted configurations. The actuation member 108 can be disposed on the proximal portion of the suture delivery device 100, which can facilitate handling of the actuation member 108 outside the patient's body. By way of non-limiting example, the actuation member 108 can be a button, a switch, a slider, a knob, etc., although in the illustrated embodiment the actuation member 108 is a plunger slidably disposed within the handle 112. As shown in FIGS. 3 and 9, the actuation member 108 is a generally elongate member with a circular cross-section, but the actuation member 108 can be of any shape suitable for manual actuation. The actuation member 108 can be formed from a material configured to facilitate gripping by the user, and/or can have one or more features configured to facilitate gripping. In the illustrated embodiment, the actuation member 108 has a flange 156 on a proximal portion thereof to help the user advance and retract the actuation member 108. The flange 156 can also serve as a stop to prevent distal movement of the actuation member 108 beyond a desired point. For example, the flange 156 can abut the proximal-most end of the handle 112 when the suture delivery member 104 is in the advanced configuration.

Figure 10:
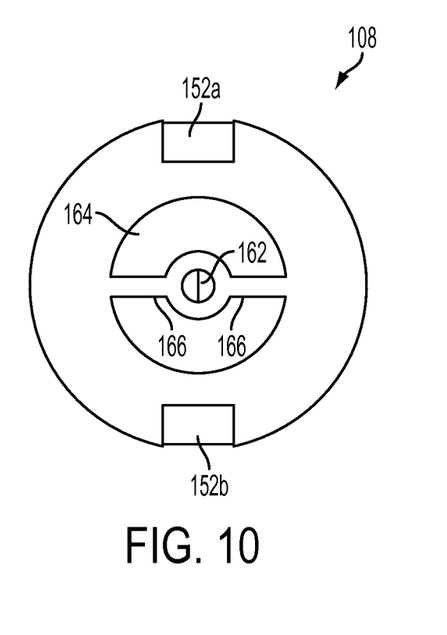
FIG. 10 is a distal end view of the actuation member of FIG. 2.

The actuation member 108 can be configured to move the suture delivery member 104 between the advanced and retracted configurations in a variety of ways. In the illustrated embodiment, the user can advance the suture delivery member 104 to the advanced configuration by sliding the actuation member 108 distally, and can retract the suture delivery member 104 to the retracted configuration by sliding the actuation member 108 proximally. Because the actuation member 108 is directly attached to the suture delivery member 104 in the illustrated embodiment, movement of the actuation member 108 directly corresponds to movement of the suture delivery member 104. In particular, the actuation member 108 can have a bore 162 suspended within a channel 164 of the actuation member 108. As shown in FIG. 10, the bore 162 is supported within the channel 164 by support members 166 extending radially inward from an inner wall of the channel 164. The bore 162 can be sized to fixedly secure any length of a distal portion of the suture delivery member 104 therein, either permanently or detachably, for example by interference fit, friction fit, snap fit, etc. Although the bore 162 of the exemplary embodiment forms a separate passageway within the channel 164, it will be appreciated by a person skilled in the art that the bore 162 and the support members 166 can be eliminated, and the channel 164 can be configured to directly attach to the suture delivery member 104. It will further be appreciated by a person skilled in the art that there can be any number of intervening elements between the suture delivery member 104 and the actuation member 108, for example a mechanism to increase or decrease force applied to the actuation member 108 and transferred to the suture delivery member 104, or to convert one type of movement of the actuation member 108 to a different type of movement of the suture delivery member 104.

As explained above, the actuation member 108 can have one or more features thereon for mating engagement with the handle 112. In the exemplary embodiment, the notches 152a, 152b are formed on opposite sides of the actuation member 108 for mating with the ridges 150a, 150b of the handle 112. The notches 152a, 152b can be of any shape, number, and size effective for mating engagement with the ridges 150a, 150b and to allow for sliding of the actuation member 108 with respect to the handle 112. In some embodiments, the notches can have one or more features thereon and/or can be formed from a material that creates friction between the actuation member 108 and the handle 112. This can help prevent the user from accidentally moving the suture delivery member 104 between the advanced and retracted configurations during surgery.

Various features can be formed on the actuation member 108 to indicate certain information to the user about the distal portion of the suture delivery device 100. For example, similar to the arrow 138 of the handle 112 described above, the actuation member 108 can have a direction indication feature, e.g., arrow 160 etched on a proximal portion thereof. The arrow 160 can indicate the direction of curvature of the suture delivery member 104 when in the advanced configuration. In particular, the arrow 160 of the actuation member 108 can be visible to the user even where the distal portion 122 of the handle 112 is inserted into the patient's body and is therefore not visible to the user. The actuation member 108 can additionally or alternatively have at least one depth indication feature, for example demarcation lines 158, which can indicate a distance that the suture delivery member 104 extends beyond the distal-most end of the shaft 114. For example, a number of demarcation lines 158 extending proximally beyond the proximal-most end of the handle 112 can indicate a certain distance that the suture delivery member 104 extends distally beyond the distal-most end of the shaft 114.

The actuation member 108 can have any length suitable for manual actuation, as will be appreciated by a person skilled in the art. Generally, however, the length of the actuation member 108 can be in the range of about 3 inches to 6 inches and a cross-sectional dimension of the actuation member 108 can be in the range of about 0.5 inches to 1 inch.

The suture delivery device 100 can include one or more locking mechanisms to lock the suture delivery member 104 in the advanced configuration, the retracted configuration, or in any intermediate configuration between the retracted and advanced configurations. The locking mechanism can be coupled to the proximal portion of the suture delivery device 100 and can include an actuator, e.g., a button, a knob, a switch, etc., configured to be manually manipulated by the user. In another embodiment, the locking mechanism can include prongs or notches spaced at intervals on the inner wall 137 of the handle 112 or along the actuation member 108, which can correspond to the other of a prong or a notch formed on the other of the inner wall 137 or the actuation member 108, thus functioning as a ratcheting mechanism to hold the suture delivery member 104 in place along various phases of advancement/retraction. For example, one or more of the demarcation lines 158 on the actuation member 108 can be notches that correspond to a circular protrusion formed on the inner wall 137 of the handle 112. In this embodiment, the user must apply a tensional force exceeding a threshold force to the actuation member 108 to disengage the notches from the corresponding prong to the next phase of advancement/retraction. The locking mechanism, by allowing for locking of the suture delivery member 104 in the intermediate configuration, can allow for the user to select a desired length of the suture delivery member 104 extending beyond the distal end of the body portion 102, thereby allowing the suture delivery device 100 to be effective in small surgical spaces and/or in crowded surgical spaces.

The suture delivery device 100 can be configured for use with various types and sizes of sutures in several ways. For example, the suture 106 can be a number 2 suture and can be of any length suitable for engaging bone and/or tissue. Any of the channel 136 of the handle 112, the channel 140 of the shaft 114, a lumen and/or channel of the suture delivery member 104, and the channel 164 of the actuation member 108 can additionally or alternatively have one or more engagement features formed therein for slidably seating the suture 106 and/or securing the suture 106 to the suture delivery device 100. In one exemplary embodiment, not shown, notches can be formed in any of the aforementioned channels along any length thereof that are sized to slidably seat the suture 106. Additionally or alternatively, a feature formed on the exterior of the suture delivery device 100 can assist in attaching a proximal portion of the suture 106 to the suture delivery device 100. By way of non-limiting example, a hook can be formed on the proximal portion of the suture delivery device 100, e.g., the handle 112, for wrapping the suture 106 therearound. Additionally or alternatively, the suture 106 can have one or more engagement features, e.g., a needle, for mating engagement with any portion of the suture delivery device 100.

The suture delivery devices disclosed herein can be generally used to pass sutures around anatomical structures. In an exemplary embodiment, a suture delivery device can be used to pass a suture around a bony structure.

In use, a suture delivery device can be inserted into a body of a patient in accord with customary surgical procedures, which can include open surgery or minimally invasive surgery (e.g., using one or more access cannulae). The suture delivery device is eventually arranged such that a distal end of the suture delivery device is positioned adjacent to a bony structure. During insertion, a suture delivery member disposed within a body portion of the suture delivery device can be in a retracted configuration, in which the suture delivery member is disposed within an elongate body portion of the suture delivery device. Using a curved distal end of the body portion as a guide, a surgeon can locate the bony structure and can align the suture delivery device such that the curved distal end of the body portion extends partially around the boy structure and such that it is oriented in the intended direction of travel of the suture. One or more direction indication features on the suture delivery device can indicate a direction of curvature of the distal end of the body portion and of suture delivery member in the advanced configuration to assist the surgeon in aligning the suture delivery device to extend around the bony structure. Once the body portion is oriented in the desired position, the suture delivery member can be distally advanced beyond a distal end of the body portion by, e.g., actuation of an actuator, to an advanced configuration, as described above, or to an intermediate configuration between the retracted and advanced configurations. The surgeon can use depth indication features on the actuation member to measure a distance that the suture delivery member extends beyond the distal-most end of the body portion in the advanced configuration or in any of the intermediate configurations. With the suture delivery member in the advanced configuration, a suture attached to the suture delivery member can be passed around the bone, in one exemplary embodiment around about at least 270° of a circle. Once the suture is disengaged from the suture delivery device, the suture delivery member can then be retracted proximally to the retracted configuration and the suture delivery device can be removed from the patient's body. Surgical repair using the delivered suture can then proceed according to accepted surgical techniques.

Figure 11:
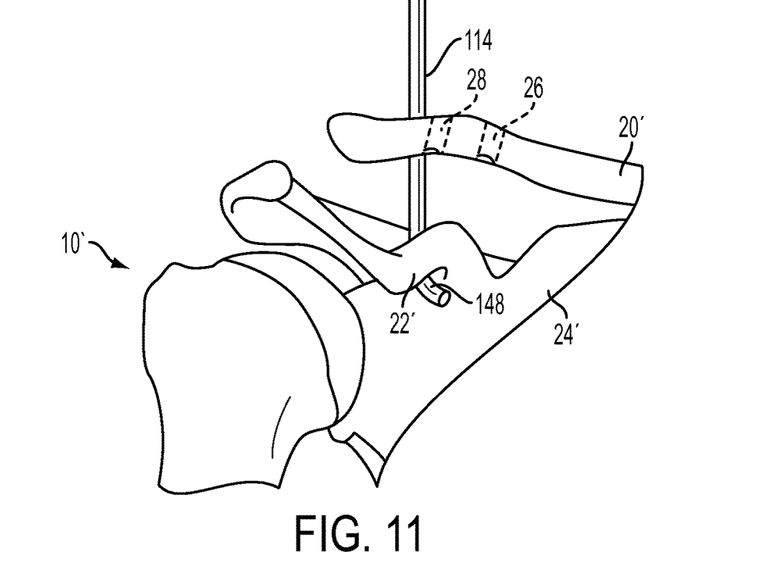
FIG. 11 is a perspective view of a step of a method for performing ACCR in which the suture delivery device of FIG. 2 is inserted into the torn AC joint of FIG. 1B.
Figure 12:
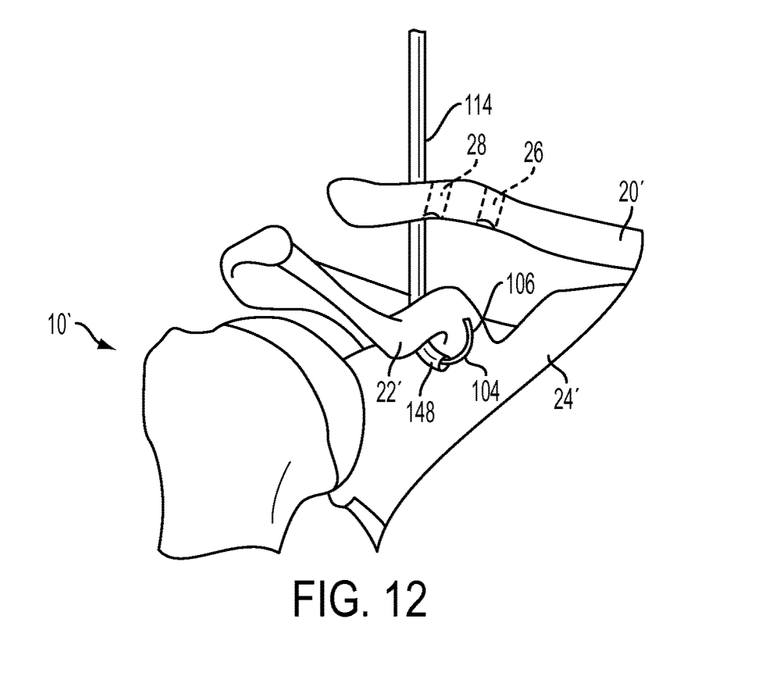
FIG. 12 is a perspective view of a step of the method for performing ACCR in which the suture delivery member of FIG. 8 is at least partially deployed from the suture delivery device of FIG. 2.
Figure 13:
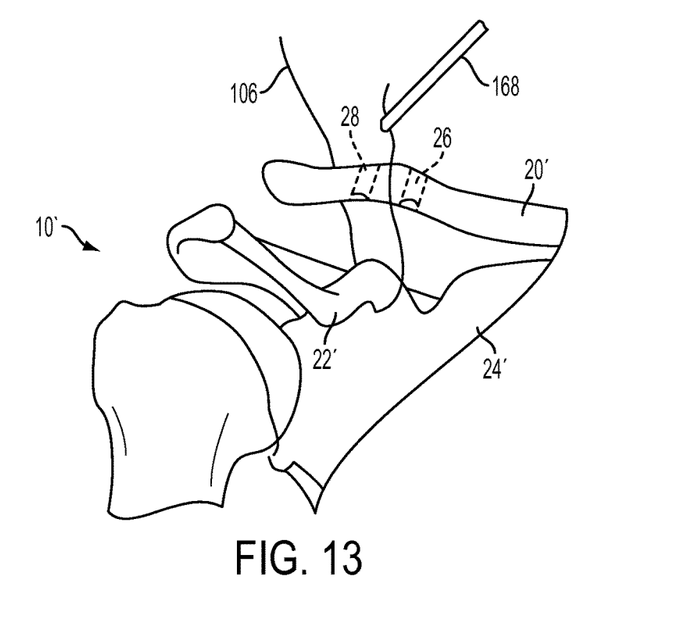
FIG. 13 is a perspective view of a step of the method for performing ACCR in which a suture grasper is used to pull a suture deployed from the suture delivery device of FIG. 2.
Figure 14:
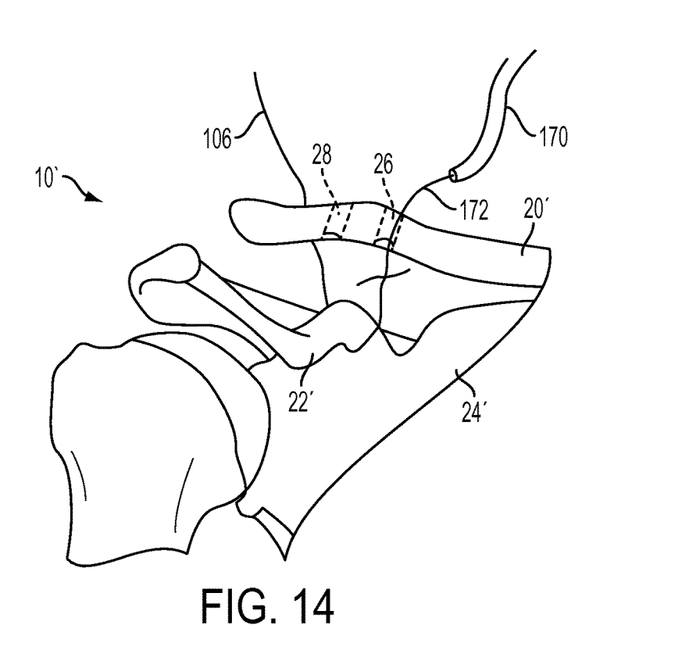
FIG. 14 is a perspective view of a step of the method for performing ACCR in which a ligament graft having a suture attached thereto is inserted into the body.
Figure 15:
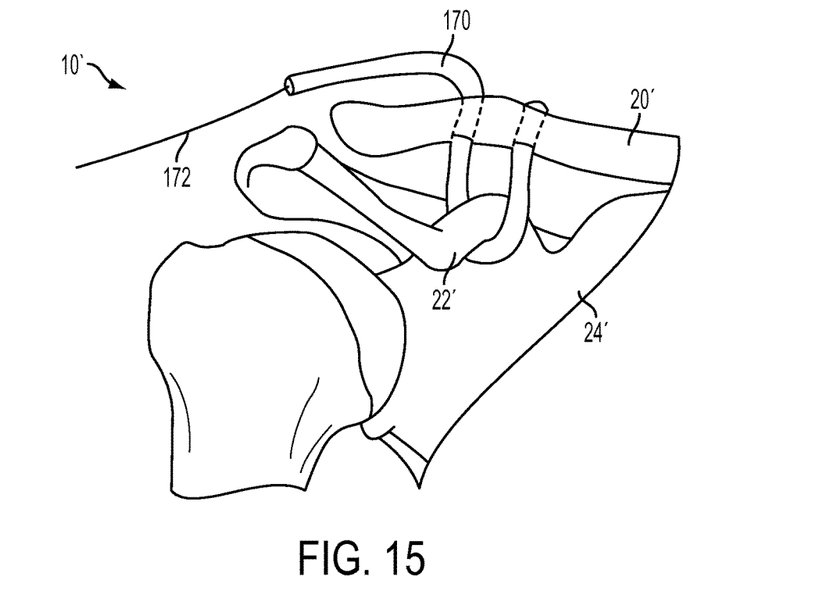
FIG. 15 is a perspective view of a step of the method for performing ACCR in which the ligament graft of FIG. 14 is pulled through holes in a bone.
Figure 16:
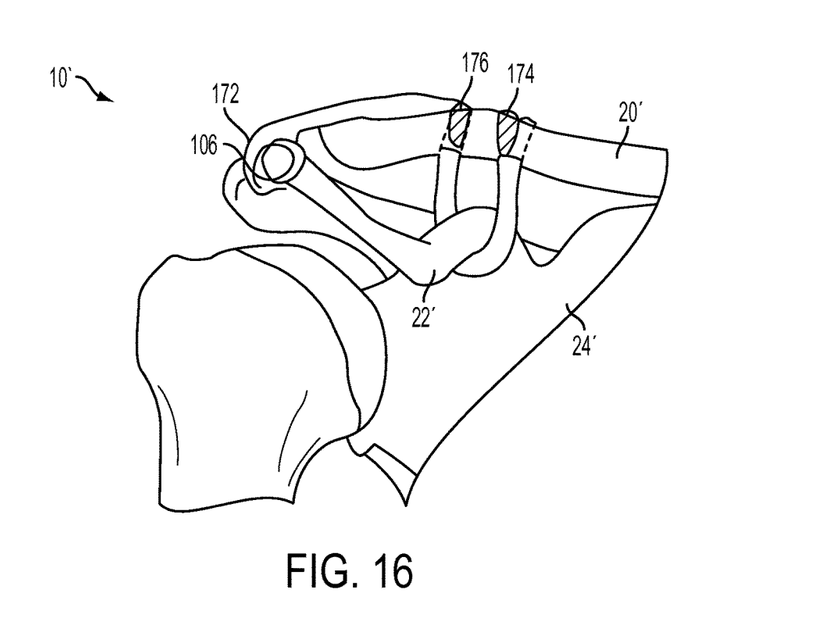
FIG. 16 is a perspective view of a step of the method for performing ACCR in which the ligament graft of FIG. 15 is secured to the bone.

The suture delivery device can be used, for example, in an exemplary ACCR procedure shown in FIGS. 11-16, which are simplified views of the anatomy of the AC joint with various soft tissue structures (including skin) removed for ease of illustration. Moreover, although cannulae for use in minimally surgical procedures are not illustrated in FIGS. 11-16 (for ease of viewing), a person skilled in the art will understand that such devices can be used in an ACCR procedure. FIG. 11 depicts the insertion of the shaft 114 of the exemplary suture delivery device 100 into the torn AC joint 10', the torn AC joint 10' having been cleared of torn ligament tissue and having had a first hole 26 and a second hole 28 drilled into the clavicle 20'. The suture delivery device 100 can be advanced, using the curved distal portion 148 of the shaft 114 to locate the coracoid process 22'. Once located, one or both of the arrows 138, 160 can indicate to a surgeon the direction of curvature of the shaft 114 and the suture delivery member 104 disposed therein, thus helping the surgeon to orient the shaft 114 distally of the coracoid process 22' and extending partially around the coracoid process 22'. The suture delivery member 104 can then be deployed to the advanced configuration, or to any of the intermediate configurations, by distal advancement of the actuation member 108, as shown in FIG. 12, such that the suture delivery member 104 and the suture 106 extend approximately 270° of a circle around the coracoid process 22'. The surgeon can measure a distance that the suture delivery member 104 extends beyond the distal-most end of the shaft 114 according to the number of demarcation lines 158 that extend proximally beyond the proximal-most end of the handle 102. A suture grasping device, e.g., forceps 168 shown in FIG. 13, can then be inserted into the AC joint 10' to grasp the suture 106 and detach the suture 106 from the suture delivery member 104. Once the suture 106 is fully detached from the suture delivery device 100, the suture delivery member 104 can be moved to the retracted configuration by proximal retraction of the actuation member 108 and the suture delivery device 100 can be removed from the patient's body. Next, a ligament graft 170 having a second suture 172 attached thereto can be inserted into the AC joint 10' and the second suture 172 can be threaded through the first hole 26. The second suture 172 can be attached to the suture 106, e.g., using the forceps 168 to tie the suture 106 to the second suture 172 with a knot, as shown in FIG. 14, and the ligament graft 170 can then be pulled along a path defined by the suture 106 and the second suture 172. Specifically, as shown in FIG. 15, the ligament graft 170 can be pulled distally through the first hole 26, looped around the coracoid process 22', and then pulled proximally back through the second hole 28. Finally, the ligament graft 170 can be secured in place by securing the suture 106 and the second suture 172 to the clavicle 20' and inserting fixation devices, e.g., screws 174, 176, into the first and second holes 26, 28, respectively. Thus oriented, as shown in FIG. 16, the ligament graft 170 can secure the clavicle 20' to the scapula 24', thereby functioning as a replacement for torn ligaments.

A person skilled in the art will appreciate that the present invention has application in conventional minimally-invasive and open surgical instrumentation as well application in robotic-assisted surgery.

The devices disclosed herein can also be designed to be disposed of after a single use, or they can be designed to be used multiple times. In either case, however, the device can be reconditioned for reuse after at least one use. Reconditioning can include any combination of the steps of disassembly of the device, followed by cleaning or replacement of particular pieces and subsequent reassembly. In particular, the device can be disassembled, and any number of the particular pieces or parts of the device can be selectively replaced or removed in any combination. Upon cleaning and/or replacement of particular parts, the device can be reassembled for subsequent use either at a reconditioning facility, or by a surgical team immediately prior to a surgical procedure. Those skilled in the art will appreciate that reconditioning of a device can utilize a variety of techniques for disassembly, cleaning/replacement, and reassembly. Use of such techniques, and the resulting reconditioned device, are all within the scope of the present application.

One skilled in the art will appreciate further features and advantages of the invention based on the above-described embodiments. Accordingly, the invention is not to be limited by what has been particularly shown and described, except as indicated by the appended claims. All publications and references cited herein are expressly incorporated herein by reference in their entirety.

What is claimed is:

1. A method for passing a suture around an anatomical structure, comprising:
   inserting a suture delivery device into a body of a patient such that a distal end of the suture delivery device is positioned adjacent to a bony structure, the suture delivery device having a handle disposed on a proximal end of the suture delivery device, and a direction indication feature formed on the handle;
   orienting the distal end of the suture delivery device based on information provided by the direction indication feature;
   advancing a suture delivery member carrying a first suture from within the suture delivery device such that the suture delivery member follows an arc defining at least about 270° of a circle to extend around the bony structure;
   manipulating the suture to engage the bony structure; and
   attaching the first suture to the second suture, the second suture attached to a ligament graft; and
   securing the ligament graft to the bony structure using the first surture.

2. The method of claim 1, further comprising, after manipulating the suture to engage the bony structure, releasing the suture from the suture delivery device.

3. The method of claim 1, wherein the bony structure comprises the coracoid process.

4. The method of claim 1, wherein the ligament graft is used to repair a torn acromioclavicular joint.

5. A method for passing a suture around an anatomical structure, comprising:
   inserting a suture delivery device into a body of a patient such that a distal end of the suture delivery device is positioned adjacent to a bony structure;
   advancing a suture delivery member carrying a first suture from within the suture delivery device such that the suture delivery member follows an arc defining at least about 270° of a circle to extend around the bony structure;
   manipulating the suture to engage the bony structure;
   attaching the first suture to a second suture, the second suture attached to a ligament graft; and securing the ligament graft to the bony structure using the first suture.

6. The method of claim 5, further comprising, after manipulating the suture to engage the bony structure, releasing the suture from the suture delivery device.

7. The method of claim 5, wherein the bony structure comprises the coracoid process.

8. The method of claim 5, wherein the ligament graft is used to repair a torn acromioclavicular joint.

* * * * *